United States Patent [19]
Liu et al.

[11] Patent Number: 5,456,114
[45] Date of Patent: Oct. 10, 1995

[54] ELASTIC WAVE SENSING SYSTEM

[75] Inventors: Yi Liu, Acton; Lawrence C. Lynnworth, Waltham, both of Mass.

[73] Assignee: Panametrics, Inc., Waltham, Mass.

[21] Appl. No.: 52,159

[22] Filed: Apr. 23, 1993

[51] Int. Cl.$^6$ .................................................. G08B 17/12
[52] U.S. Cl. ...................... 73/597; 73/290 V; 73/61.79; 73/64.53; 73/861.18
[58] Field of Search .......................... 340/621; 73/290 V, 73/597, 599, 61.79, 64.53, 82 A, 861.18

[56] References Cited

U.S. PATENT DOCUMENTS

| | | | |
|---|---|---|---|
| 4,118,983 | 10/1978 | Braznikov | 73/290 V |
| 4,248,087 | 2/1981 | Dennis | 340/621 |
| 4,320,659 | 3/1982 | Lynnworth et al. | 73/589 |
| 4,461,178 | 7/1984 | Chamuel | 73/599 |
| 4,838,127 | 6/1989 | Herremans | 73/642 |
| 5,159,838 | 11/1992 | Lynnworth | 73/644 |

OTHER PUBLICATIONS

Ageeva, N. S., Ultrasonic Method for Measuring the Height of the Fluid Level in a Vessel by Means of Flexural Oscillations of a Thin Elastic Strip, Acoustics Institute, Academy of the Sciences of the USSR, Moscow, Jan.–Mar., 1960, vol. 6, No. 1 pp. 120–121.
Dieulesaint et al., A Guided Acoustic Wave Liquid Level Sensor, 1987 IEEE Ultrasonics Symposium, pp. 569–572.
Royer et al., Remote Sensing of the Thickness of Hollow Cylinder From Optical Excitation and Detection of Lamb Waves, 1989 IEEE Ultrasonics Symposium (first page).
Lynnworth, L., Flexural Wave Externally–Attached Mass Flowmeter for Two–Phase Fluids in Small–Diameter Tubing, 1–MM ID to 16–MM ID, 1990 IEEE Ultrasonics Symposium.
Royer, D., et al., Capteurs `a ondes élastiques guidées, J. Phys. III France 2 Jan., 1992, 145–168.

Primary Examiner—Hezron E. Williams
Assistant Examiner—Christine Oda

[57] ABSTRACT

A sensing system detects elastic waves propagated along a sensing path in a sheet to detect a characteristic of material contacting the other side of the sheet. An acoustic load applied between transducers discriminates characteristics in diverse environments. Different systems detect density, stiffness, presence, degree of coupling, thickness, or fill height of the material, with applications to areas as diverse as aircraft wing ice measurement, storage tank fill height detection, and mass flow detection. In one preferred embodiment a protective housing covers and protects the first side of the sheet over a region of the sheet encompassing the sensing path, and may secure transducers in defined positions. The housing preferably defines a closed reservoir that is temporarily filled to determine a normative measurement such as transit time or change in phase velocity. The normative measurement provides an empirical calibration that, in turn, allows a final parameter or a detection threshold to be precisely determined.

21 Claims, 12 Drawing Sheets

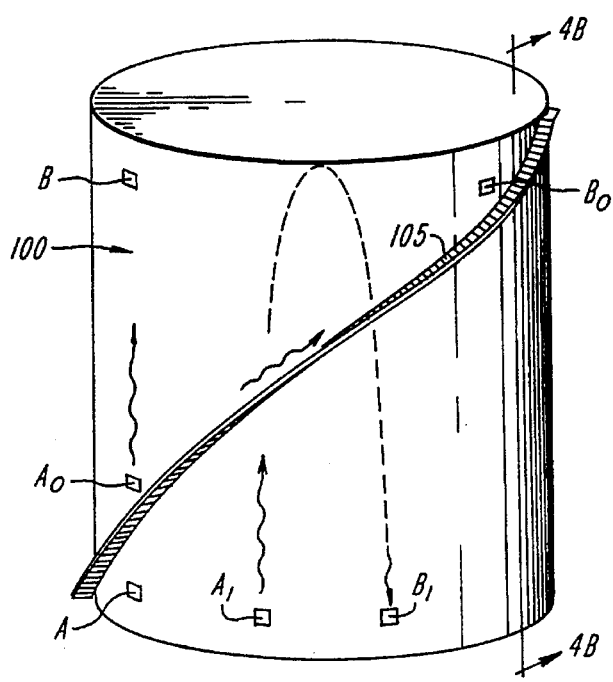
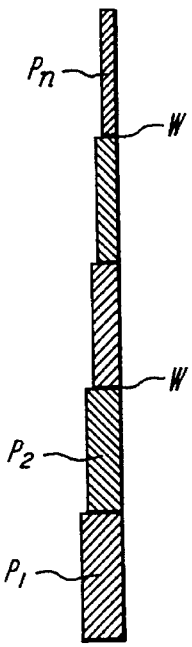
FIG. 4A  FIG. 4B
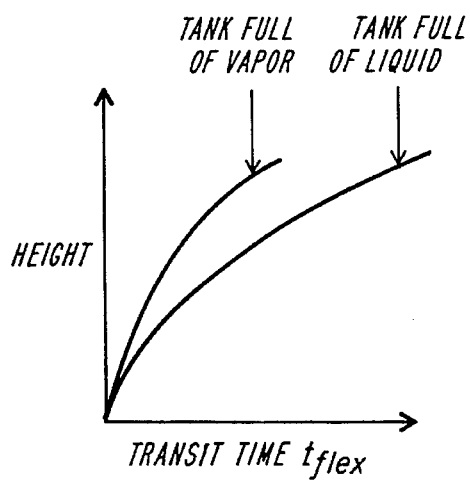
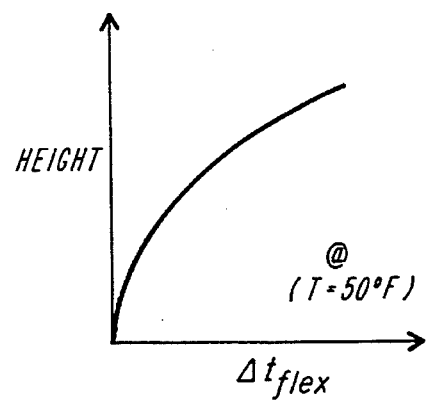
FIG. 4C  FIG. 4D

ELASTIC WAVE SENSING SYSTEM

BACKGROUND OF THE INVENTION

The present invention relates to acoustic sensing and measurement systems, and particularly to systems which detect the presence or a specific property of material bounded by a wall. Examples include systems for sensing liquid level and interfaces in a tank, fluid flow in a conduit, or the presence or thickness of ice built up on a hull, wing or fuselage.

Extensive technologies have been developed to measure flow rate, mass flow rate, or related parameters such as density or temperature, for fluids contained within conduits, by propagating ultrasonic waves along a path through the fluid, and measuring transit time, Doppler shift or other characteristic of the interaction of the signal with the fluid.

In many of these applications, while certain corrections must be made in the initial set up or subsequent signal processing to account for the effects of transducer mounting and housing geometry, the basic processing involves the measurement and comparison of ultrasonic signals propagating through a fluid. See, for example, U.S. Pat. No. 4,787,252 of Saul A. Jacobson et al. In other systems, wave energy may be propagated through a specially shaped wave guide, and the properties of the interrogating wave are affected by an interaction of the wave guide with a fluid that fills or surrounds the wave guide. U.S. Pat. No. 4,893,496 of Haim H. Bau et al. shows a system of this latter type, in which a polygonal or other specially shaped rod or cylinder is excited by a torsional wave, and coupling of energy from the rod or cylinder into an adjacent fluid provides a direct indication of the magnitude of the fluid's density or viscosity. In systems of this type, the wave is guided by the solid body, and its propagation is affected by energy coupling with the adjacent fluid.

It has also been suggested to use specialized systems of various kinds with flexural wave excitation to measure a static condition such as fluid height or ice covering.

In particular, work has been done in France by Dieulesaint on a fluid sensor in which a tube extends down into the fluid and is excited at one end with a flexural wave that is reflected at the air/fluid interface and then detected. The relatively slow propagation speed of a flexural wave in a long tube (or thin strip according to a method reported by Ageeva in 1960) allows resolution of the fluid level height.

U.S. Pat. No. 4,461,178 of Jacques Chamuel shows a method of detecting ice accumulations and the degree of attachment of ice formed on an aircraft wing. That system uses acoustic signals that propagate in both compressional and flexural modes through a sheet forming a surface of the wing. The patent reports that amplitude of the flexural wave varies with surface deposits, while the compressional mode propagates through the sheet unattenuated, and can therefore be used to normalize the amplitude of the received flexural wave signal.

In general it may be said that the systems of this latter type, involving the interaction of a flexed body with a surrounding material, appear to be rather specialized, and while distinct qualitative effects have been observed on the guided flexural wave signal, such systems do not have the well-developed theoretical models enjoyed by more conventional systems that employ unguided waves propagated through the fluid itself. Their teachings accordingly are limited to rather specific constructions.

It is therefore desirable to develop a more general wave detection or measurement system for elastic waves in sheet structures such as conduit, tank or vessel walls.

It is also desirable to develop an elastic wave system that is not restricted to use with customized or particular sensors, conduits or containment vessels.

SUMMARY OF THE INVENTION

These and other desirable features are achieved in accordance with the present invention by providing one or more transducers for generating and detecting elastic waves in a sheet or wall bounding a body of material which is to be detected, processing the detected signals to make a determination, and optionally selectively applying an acoustic load to the wall for generating a reference determination. The wall may be the wall of a pipe or conduit, a surface of an airfoil, hull or fuselage, or the wall of a container such as a storage tank.

In a preferred construction, a housing mounts on the wall and holds at least one transducer in acoustic contact to the wall such that actuation of the transducer delivers a compressional wave impulse normal to the wall and initiates propagation of a flexural wave therein. The housing protects the wall from adventitious environmental loading, and together with the wall forms a closed cell. Means are provided to fill the cell with liquid at selected times, thereby placing an acoustic load on the outside of the wall. A reference determination of the flexural wave propagation characteristics is made with the outside of the wall in contact with this liquid. The liquid is then drained and the unperturbed propagation characteristic determined. A comparison of flexural wave propagation with and without the acoustic load normalizes the detected phase velocity over a wide operating range, and allows use of the system in sensing environments for which complete modeling or sensing of additional parameters to determine expected signal propagation characteristics, would be impractical.

In specific embodiments of the invention, the system may be used to detect ice buildup on a vessel skin, may be configured to measure height or actuate an overflow alarm in a storage tank, a high pressure alarm or overflow alarm in a pressure vessel, or to measure characteristics such as fluid pressure in a standpipe. Clamp-on embodiments are adapted to directly measure fluid density, flow rate or both in conduits.

BRIEF DESCRIPTION OF THE DRAWINGS

These and other features of the invention will be understood from the following description, taken together with drawings of illustrative embodiments and principles of operation, wherein:

FIGS. 4A–4D illustrate another tank sensing embodiment;

DETAILED DESCRIPTION OF INVENTION

Figure 1:
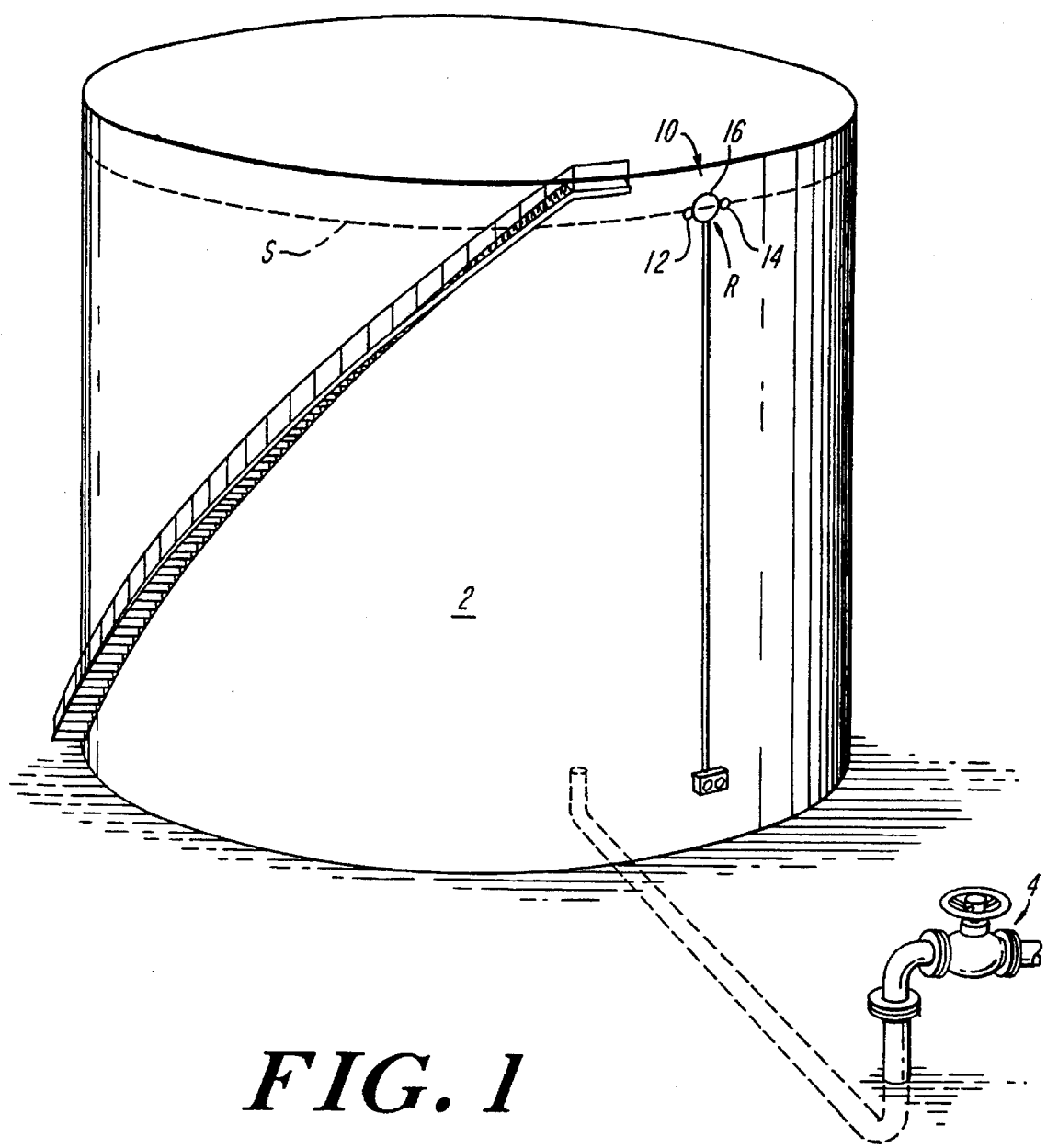
FIG. 1 shows one embodiment of an acoustic sensing system in accordance with the present invention.

FIG. 1 illustrates a flexural wave sensing system 10 in accordance with the present invention, illustratively installed on a liquid storage tank 2 such as a fuel oil storage tank. By way of example, such tanks may be formed of steel plate approximately one centimeter thick, which is riveted or welded into a cylindrical structure three to fifty meters in diameter and ten to fifteen meters tall. The plates may be eight feet tall and are successively (stepwise) thinner towards the top of the tank, diminishing to approximately 5 mm thickness for the uppermost plates. Such tanks are filled via a fixed conduit 4, to a maximum fill height S, a short distance below the top of the tank. Various forms of floating covers or seal structures are employed on these tanks, rather than a closed roof, so as to avoid having a fume-filled dead space above the liquid, which could lead to explosion. These cover assemblies may involve seals, bumpers or scrapers for contacting or sealing against the inner wall of the tank. As discussed further below, these elements can be remotely detected by sensing systems of the present invention. However, in one aspect of this embodiment of the invention a sensor system 10 detects the presence of fluid in the tank at the fill level S, and thus acts as an overflow warning system.

Sensor system 10 comprises a pair of transducers 12, 14 on opposite edges of an enclosed surface region R that defines a signal propagation path at the specific fill height S at which it is desired to detect liquid in the tank. The region R is enclosed with a bounding frame or housing denoted generally by 16, which is formed of a thin steel hoop of L-shaped cross section, the L profile providing a first face for fastening flat against the tank wall, and a second face perpendicular thereto extending outwardly from the wall. Transducers 12, 14 are each mounted on the first face and are acoustically coupled to the tank wall, while the frame forming the thin steel hoop defines a fixed spacing between the two transducers.

Figure 2:
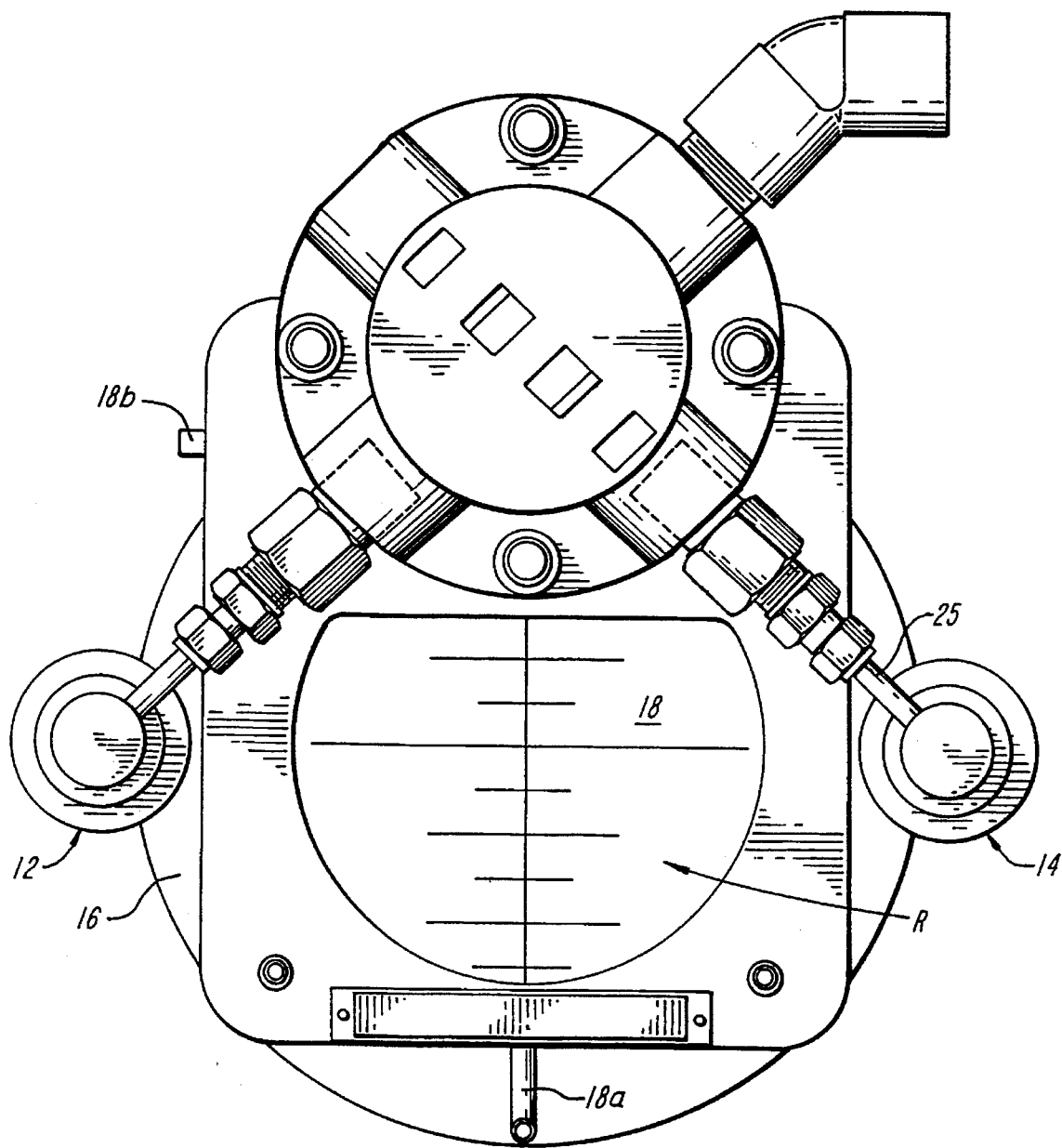
FIGS. 2 and 3 illustrate details of the system of FIG. 1.
Figure 3:
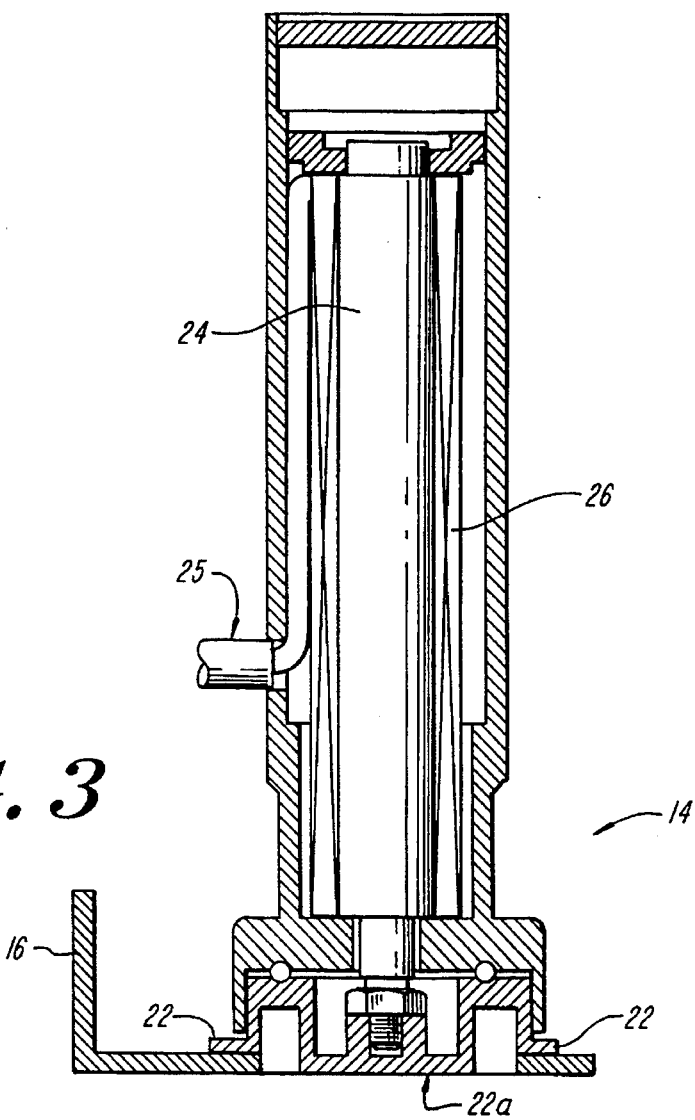

According to a principal aspect of the invention, frame 16 has a cover so that it also defines an enclosed volume over the region R, best seen in FIGS. 2 and 3. The volume is bounded by frame 16 and the cover member 18, thus forming a fluid reservoir over the surface region R. The frame 16 is hermetically attached to the tank wall, by solder, epoxy, adhesive or the like, so that the tank wall forms another bounding surface closing the reservoir thus constituted.

As seen in FIGS. 2 and 3, frame 16 is formed of a relatively thin material, for example, an eighteen to twenty-two gauge sheet steel, that allows it to conform accurately to the walls of the tank without being so thick that it affects the overall mass or stiffness of the tank wall in the vicinity of the interrogation region, and to avoid the introduction of an interfering acoustic path between transducers. A threaded contact assembly 22 machined from bar stock is welded to the frame 16 at two diametrically opposed positions, and includes a machined stainless steel button 22a that protrudes a few thousandths of an inch toward the plane of the wall and defines a contact acoustic coupling at normal incidence for coupling acoustic signals into the wall. Various additional spacers, packing and grounding or shielding elements, not specifically numbered, are shown to illustrate an explosion-proof transducer which is suited for fuel tanks. All tolerances are kept small to control any flame paths from or through crucial elements.

In the illustrated embodiment, a magnetostrictive rod 24 of nickel or Remendur material screws into the contact button 22a, and is surrounded by a solenoid coil 26 which is actuated by an electric current signal burst through electrical conduit 25 to generate compressional waves in the rod. These waves travel along the rod into the contact button, and produce a momentary motion of the tank wall normal to the surface. After traveling to the other side of region R the flexural wave is reconverted to a compressional wave in a second rod having a corresponding pickup coil. Preferably, the transmitting coil 26 has a low number of turns of low gauge wire, to accommodate a high current drive signal, for example a 0.3 ampere signal burst at a level of ten volts. The pickup coil, on the other hand, has many turns of high gauge wire to constitute a sensitive receiver with a high voltage output for detecting attenuated waves. By using a straight rod with one end free as λ4 resonator, the projection of the rod perpendicular to the tank surface is minimized.

The frequency of the compressional wave is selected to efficiently convert to a flexural wave that is propagated efficiently along the steel plate wall. Typically, a frequency of about five to twenty-five kHz is appropriate for a thick steel plate wall. (A frequency of 12.5 kHz is preferred for steel plate about 5 mm to 6 mm thicknes, which is the thickness often encountered near the top of storage tanks, at the "high" or "high-high" fill levels S. The "high-high" alarm level, indicated schematically in FIG. 1, is generally set in relation to pump capacity, at approximately five minutes before overflow, typically at a height corresponding to 95% full.

According to a principal feature of this aspect of the invention, the phase velocity of the flexural wave travelling in the wall is measured to detect the presence of material, e.g., fuel oil, against the surface of the wall opposite to the surface contacted by the transducers 12, 14. Specifically, the transit time between launching of a compressional wave from rod 24 into the wall, and the reception of a delayed replica in a second rod increases when the fluid in the tank 2 reaches the height of region R, and this delay from a nominal transit time is detected to provide an indication of fluid height. In preliminary measurements on test systems, a transit time increase of over ten microseconds was observed with a transducer separation of about twenty centimeters on a steel tank of between one-half and one centimeter thickness. These transit time increases are not dependent on the quality of coupling or bonding of the transducers to the tank, and thus provide an advantage as a transit-time-based system, over amplitude-based determinations of liquid level as previously applied, for example to tanks in the method of Lynnworth, Seger and Bradshaw, U.S. Pat. No. 4,320,659 (1982).

A brief theoretical discussion of the properties of structural elastic waves—primarily Lamb waves in this context—will aid in understanding further aspects and preferred embodiments of this invention.

In general the sound speed of an elastic or acoustic wave propagating in a solid sheet will be proportional to the square root of the ratio of stiffness to density:

$$c \propto \sqrt{\frac{\text{stiffness}}{\text{density}}}.$$

Applicant has found that for a tank filled with a liquid, the presence of liquid against the tank wall, at least at low heads, operates analogously to increasing the density, thus decreasing the flexural wave propagation speed. In the case of ice built up on the exterior of a sheet structure, such as a wing or hull, that is formed of a metal denser than the ice, the primary effect is to increase the stiffness, increasing the propagation speed. In the case of granular or unconsolidated solid material bearing against the wall, such as occurs for example in a hopper or silo, there is no cohesive coupling between the wall and the material, and the principal effect on wave propagation is one of amplitude damping.

Beyond these observations further factors enter into the consideration of a measurement system according to different aspects of this invention.

It is preferable that the transducers be actuated at a frequency that corresponds to a lower order flexural elastic wave of the wall or sheet structure, most preferably to the lowest order flexural wave $a_0$, or to a frequency that is less than the cutoff frequency of a second or higher order mode. By avoiding higher frequencies in the range of these higher modes, complications from surface leakage, reflection and multimode propagation at several different phase velocities do not appear in the received signal. For a tank formed of thick steel plate, frequencies in the range of five to twenty-five kHz are suitable, whereas for detecting ice on a thin stiff aluminum or alloy aircraft skin, frequencies of about one hundred kHz are considered appropriate.

To elaborate on the surface leakage consideration, applicable when using a plate wave to sense liquid in a tank or container, coupling of the flexural wave energy into the fluid will attenuate the amplitude of the flexural wave, and complicate or even defeat measurement. To reduce this problem, the transducer or impulse initiator is driven at a frequency for which the flexural wave phase velocity in the sheet structure is less than the propagation speed of the compressional wave in the material bounding or contacting the sheet, which is to be measured. An interesting aspect of the invention described below is a flexural wave sensing system that detects fluid flow through PVC pipe of low stiffness and low density (approximately equal to 1 g/cm$^3$) using an excitation of 12.5 kHz. As in the other embodiments of this invention, the flexural wave is propagated in the wall itself rather than through the fluid within the conduit, so that transducer setup is simply a matter of spacing along the conduit, and requires no computation of liquid or wall refraction angles to make meaningful measurements. In this case, the 12.5 kHz frequency is selected to minimize radiation of energy from the light weight plastic wall into the fluid.

Another consideration occurs when "high" and "high-high" levels $S_1$ and $S_2$ are to be monitored, where $\Delta S = S_2 - S_1$ is less than a foot or so. In this case a preferred sensor assembly spans both heights with several transducers arranged to interrogate along two paths, one at height $S_1$, the other at $S_2$.

Returning now to FIGS. 1 to 3, applicant has found that for the transducer arrangement shown therein mounted on a large fluid tank with thick steel plate walls, the signal transit time between transducers 12, 14 remains essentially constant until the fluid level rises within a few inches of the horizontal centerline of the frame assembly. Thereafter, the transit time starts to increase as the tank is further filled, with the increment $\Delta t$ increasing to a maximum value of about sixteen to twenty microseconds once the top of the frame is reached. The increase is linear in the immediate vicinity of the horizontal centerline between the transducers, i.e., within an inch or two above and below the centerline. This transit time increment depends on and is approximately proportional to the fluid density, the sixteen microsecond figure being obtained with fuel oil having a density of about 0.8 g/cm$^3$, while a larger figure corresponds to a fluid such as water of greater density. By filling the reservoir in frame 16 so that the transducer side of the wall is also in contact with fluid, the increment $\Delta t$ is approximately doubled, depending in part on the density of the "calibrating" liquid compared to the liquid inside the tank. One can select a calibrating liquid that yields the same $\Delta t$ as produced by the actual liquid when both are at the level S.

According to a principal aspect of a method according to the present invention, the symmetry, or additivity, of $\Delta t$ with respect to fluid loading on the inside or the outside of the wall, is used to determine a normative transit time measurement that enables precise measurement of fill height. This is achieved as follows.

Mounted on the reservoir 16 is a fill valve assembly having a pair of electrically actuated valves connected to fluid fill and vent lines, 8a, 8b through which the reservoir may be filled, bled and drained. As noted, plate waves propagate in the wall with a speed dependent on the stiffness and density of the wall. However, variations in the transit time may be expected due to temperature changes, or due to scale, paint or other accretions on the tank wall, structural stresses and other extrinsic factors or events. Thus to reliably detect $\Delta t$, which is no more than a few percent of the nominal transit time, some normalizing measurement is desirable. Such a measurement is obtained in accordance with this aspect of the invention by filling the reservoir with a reference liquid (e.g., fuel oil, alcohol or water), measuring the transit time, draining the reservoir, then repeating the transit time measurement. The reference liquid preferably is non-toxic, non-residue-bearing and non-flammable, and may have rheological properties like those of the actual liquid. Furthermore the reservoir preferably extends more than about an inch out from the wall. Under these conditions, contact with fluid on the outside of the wall may be expected to cause the same amount of delay as rising fluid on the inside of the wall, so the difference between two consecutive measurements, made with the reservoir full and empty, of flexural wave transit time, $\Delta t_{ref}$, provides a threshold time change which may be used to trigger an alarm as the tank level rises past the sensor assembly. When the reference fluid is the same as the material in the tank applicant has found that the $\Delta t_{ref}$ closely provides the time threshhold indicative of the tank reaching its fill height S. When the reference fluid is different (e.g., water instead of fuel oil) it provides a $\Delta_{ref}$ which, scaled by an empirically determined proportionality factor $k_{ref}$ provides a full scale threshold value for $\Delta t$ fluid.

This verification procedure can also be conducted manually, by providing a small (e.g. one liter) container of calibrating liquid such as alcohol either temporarily or permanently connected to the reservoir by a flexible tube or a pipe, and manually elevating the container until the level inside the reservoir reaches S. The reservoir in this case preferably has a vent. During the intervals between verification, the fill and vent ports are covered with caps or screens if the calibrating fluid container is removed.

Figure 3C:
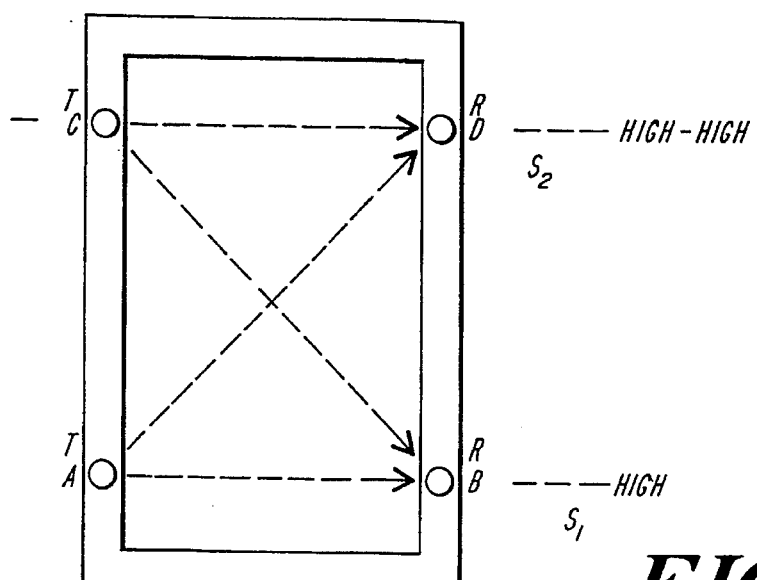
FIGS. 3B and 3C show another embodiment similar to that of FIG. 1.
Figure 3A:
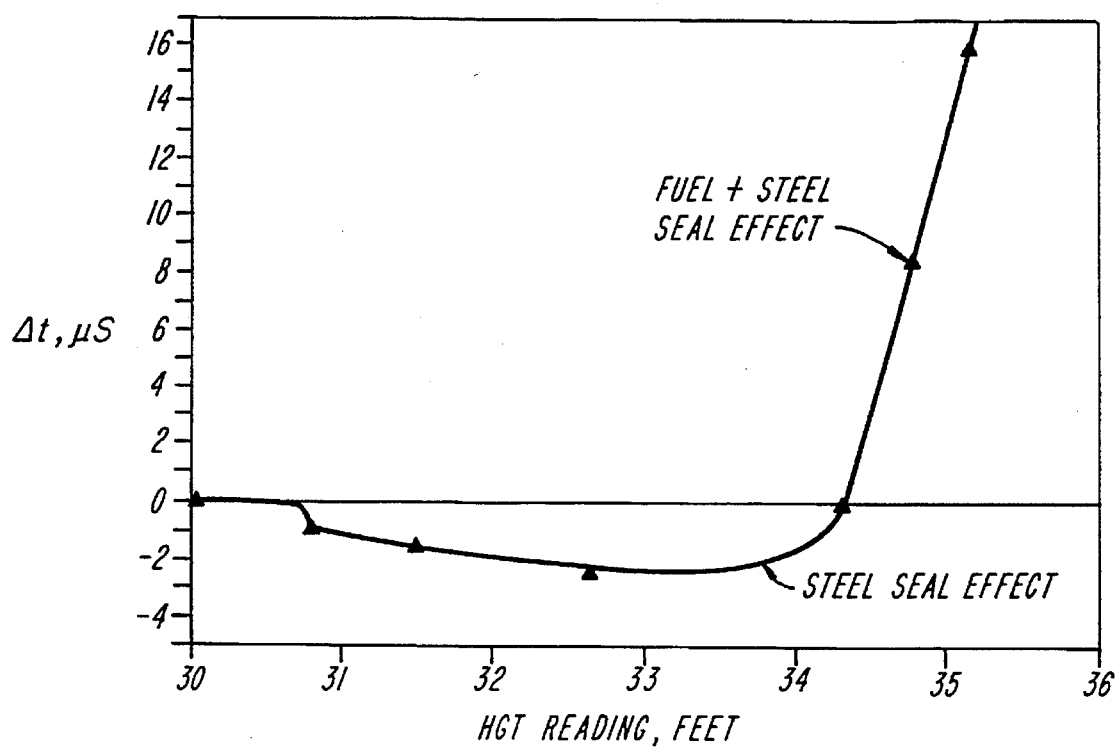
FIG. 3A is a graph of propagation time for a system as shown in FIGS. 1–3.

FIG. 3A illustrates the change Δt in transit time as a fuel oil tank was filled up to and slightly above the flexural wave sensor cell of FIGS. 1–3 mounted at the fill height of thirty-five feet on the tank. The tank had a smooth shoe seal, a construction wherein a sheet steel sealing ring or band several feet tall is mounted on a floating lid and urged outwardly against the inside of the tank wall by weighted pantograph hangars. As shown in FIG. 3A, initially the flexural wave transit time decreased by several microseconds as this metal band passed the sensing unit 16. Thereafter, as the fuel oil rose above the level of the sensors against the inside wall, transit time progressively increased, linearly with height up to a maximum delay of seventeen microseconds over the twenty centimeter path, which was reached when the level of adjoining fluid had risen to fully cover the sensor and reservoir frame.

Other forms of the tank roof which may be encountered in the field, for example ones using resilient foam sealing blocks, may be expected to show different Δt anomalies, such as increased attenuation, as the seal portion rises adjacent to the flexural wave sensing cell. In each case, however, once the fluid level contacts the side of the wall opposed to the transducers, the characteristic increase in transit time is readily detected.

It will be appreciated that large, above-ground fuel tanks as described are in general filled through fixed pipes at a pumping rate of several hundred to several thousand gallons per minute, and that it is desirable to fill each tank as full as possible, without risking overflow. If the fill sensor should fail, the risk of overflow is great. Accordingly it would be highly advantageous if the flexural wave sensing assembly were able to not only discern when the fluid has reached a height S (as evidenced, for example by a transit time increase of over ten microseconds), but also to indicate the exact height to an accuracy of about one inch, an increment that corresponds to a volume of about one thousand gallons of fuel for a sixty-foot diameter tank.

The foregoing description has special reference to a discrete fill height level detector on massive outdoor storage tanks, an application in which it is feasible to perform a Δt measurement, between transit time with the tank not entirely full and, a few minutes later, full.

However, as indicated in FIG. 3A, the phase delay is a highly linear function of fluid height in the neighborhood of a horizontal interrogation path between two transducers. Thus the basic flexural wave interrogation cell of FIG. 2 may be modified to provide not just a discrete sensor at one height, but a unit that detects the fluid at both the high level $S_1$ and the high-high level $S_2$, as well as continuously in between.

Figure 3B:
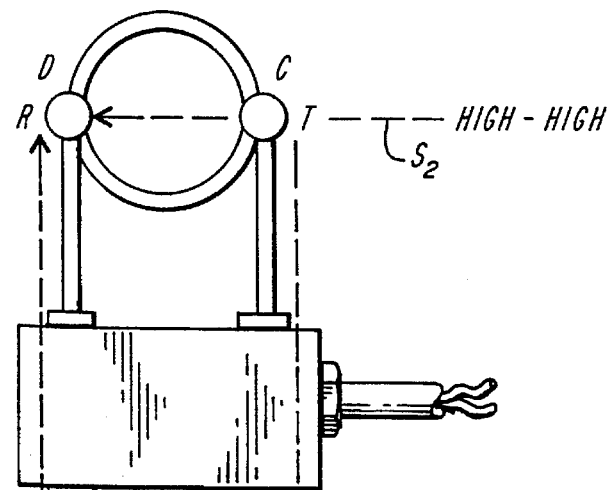
Figure 3B:
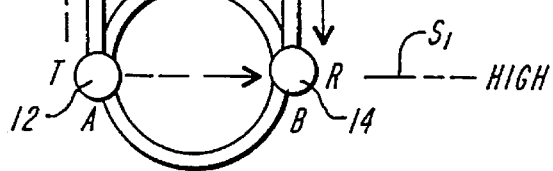

FIGS. 3B and 3C are schematic illustrations of such sensor assemblies. FIG. 3B shows four transducers A, B, C, D of either transmitting type (T) or receiving type (R). Each pair AB or CD belongs to a single assembly of the type shown in FIG. 2, which is placed at height $S_1$ or $S_2$. However, the electrical lines and actuating sequence are controlled to provide one or more vertical paths between transducers of two different assemblies. The signal along these paths varies continuously with fill level over a range of a foot or more. FIG. 3C shows a related arrangement, wherein four transducers are mounted in a single reservoir/ housing that spans the full distance from $S_1$ to $S_2$. This FIGURE also illustrates diagonal propagation paths, rather than vertical ones.

Applicant has further found that flexural wave propagation in large storage tanks yields well-defined signals over path lengths of ten meters or more, so the same equipment may be used to detect, not just the local crossing of an overflow threshold, but the fill level at arbitrary heights within the tank. In this case, Δt is preferably determined by measuring the actual transit time over the fill height path, and comparing it to a pre-compiled table of propagation times in an empty tank. In this case, the greater the portion of the tank that is filled with fluid, the longer the increment Δt will be.

FIG. 4A illustrates a tank 100 with several different possible transducer placements for a continuous level sensing system according to this aspect of the invention. Sending transducer A and receiving transducer B may be located near the bottom and top of the tank, or vice versa, to provide a single long sensing path. Alternately, a pair of transducers $A_o$, $B_o$ may be placed in helically offset positions paralleling the tank's spiral staircase 105 (FIG. 2) to span the tank height without loss of generality. Placement above or below the staircase depends on access and code requirements so that safe use of the staircase is not compromised. Another implementation is to place two transducers $A_1$, $B_1$ at the same level; in this case a pitch/catch signal path is used, with a flexural wave traveling up to the top of the tank and returning down to the receiving transducer. An external cover/reservoir may extend over the entire path. With a transducer of suitable transmit/receive characteristics, a system may also employ a single transducer positioned at the bottom (or top) of the tank which launches a signal and receives its reflection.

FIG. 4B illustrates a vertical section taken through a typical storage tank wall. As shown, the wall is formed of steel plates $P_1$, $P_2$ ... $P_n$, each successive one thinner than the next lower one, the plates being butt welded to each other to form a stepwise tapering stack with the outside wall forming a straight smooth vertical surface. Each butt weld W introduces a small reflection of the flexural wave, which may be processed to provide distance or speed calibration, since the distance between welds is known with great accuracy.

FIG. 4C shows the long path transit time of a flexural wave transmitted in the tank wall when the tank is empty (left curve) or full (right curve). The speed is constant in each plate, forming a piecewise linear function due to the stepped thickness of the plates. FIG. 4D illustrates the difference function Δt between full and empty transit times. As shown, the difference effect becomes more pronounced as the plates get thinner near the top of the tank.

The signal burst used to make transit time measurements in steel storage tanks in the manner described above may be repeated five or ten times per second, to make a number of measurements that are averaged or otherwise processed to determine a statistically reliable measurement result. Applicant has found that each short burst is audible at a distance and is a quite distinctive tapping like the chirp of a cricket. In one preferred tank measurement system according to the present invention, this distinctive sound is used as a coded condition alarm so that a person walking near the tank (or, more usually, group of storage tanks, referred to as a tank farm) can "hear" the existence of an alarm condition in a particular tank by the fact that its measurement transducer is operating at an abnormal pulse repetition rate.

This is accomplished by providing a transducer actuator circuit that drives the transmitter at any of a number of different pulse rates, e.g., 2, 5, 10, 15, or 20 bursts per second or other time interval. The processor output, in turn may distinguish the received signals as indicating one of several discrete conditions such as near empty, part full, high, or high-high. The condition code is applied to the pulse rate selector to jump the pulse rate to a higher rate when the fill level reaches a higher condition. With this arrangement, a person at the fill pipe gate valve can hear the chirps shift, e.g., from five, then ten, then fifteen chirps per second as the fill level rises from partial to high, to high-high. Furthermore, a high chirp rate at one tank is readily heard even when surrounded by a large number of tanks that are polling at lesser rates. Thus, the sensing system, when energized on one or more tanks, serves as a quick, non-invasive and easily monitored alarm system. Also, the highly directional nature of the transducer chirps further allows a guard or inspector to simply hear which tank is emitting the abnormal, condition sound. Thus, it provides a redundant check for the usual hard-wired connections to a central alarm display board.

Figure 4:
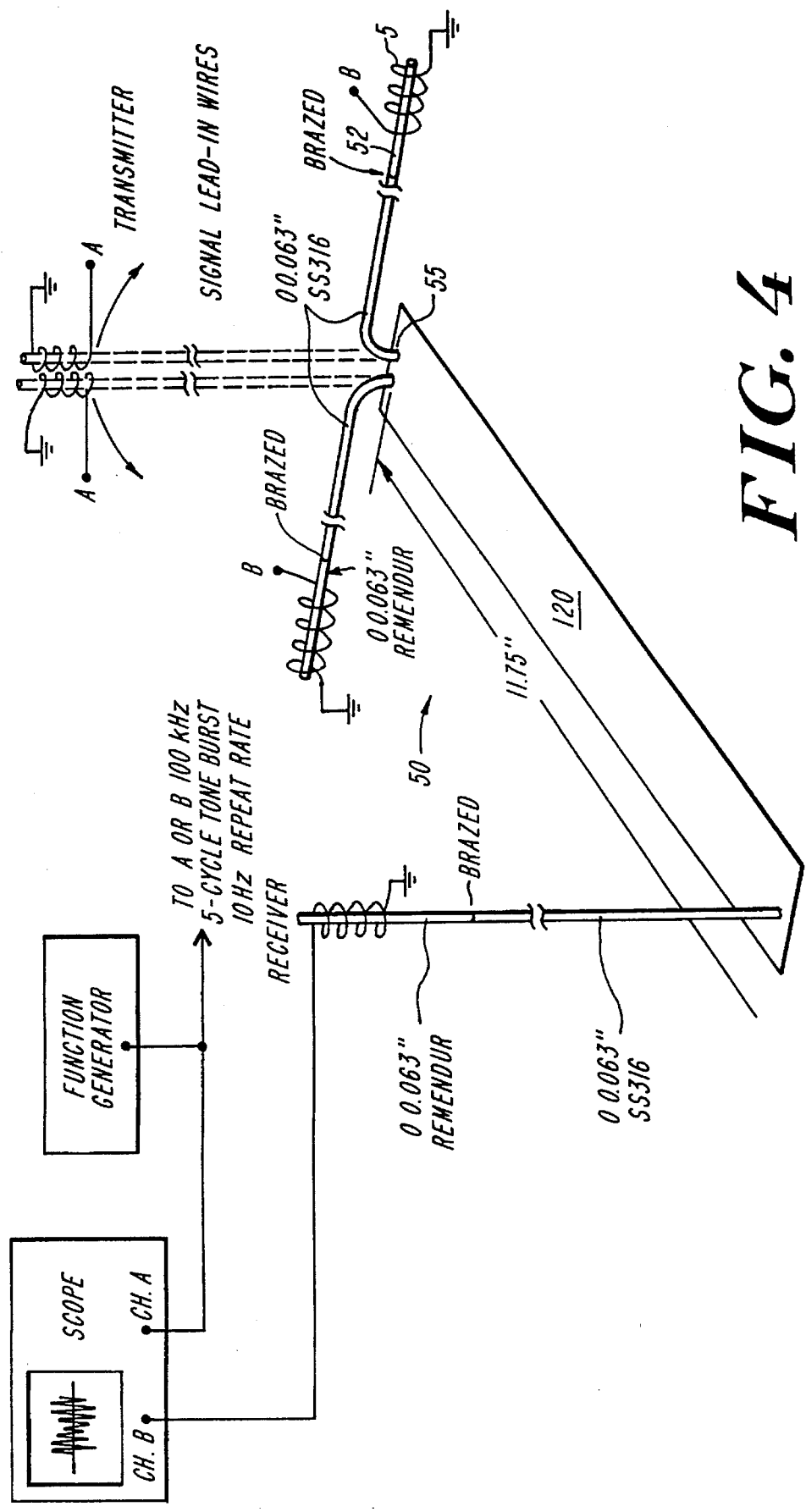
FIG. 4 illustrates another embodiment for sensing through a sheet.

Among the practical considerations in an external sensor arrangement of this sort is that of sensor integrity. Applicant has found that plate waves may be dependably launched by providing a guided compressional wave in a solenoid-driven rod. By using a curved guide rod, that has a solenoid or other actuation portion parallel to the plate, and curves at one end to contact the plate, the transducer structure may be fitted within a shallow housing or protected from stray impacts. FIG. 4 shows such an arrangement 50, with rod 52 energized by coil 54 and curving in a smooth L-shape to contact the conduit or vessel wall 120 at normal incidence at its tip 55. This configuration does not protrude far from the wall, and is less prone to damage. Further, as will be discussed below in relation to sensing of ice on external surfaces, this transducer construction may fit in small spaces, such as inside a wing or airfoil. By way of scale, the sheet contacting end may curve with a radius of curvature under an inch, with the main rod body extending only that far out from the surface.

Two sets of signal transducers are shown in the FIGURE, labeled sets A and B. Set A is a pair of straight Remendur rods, one-sixteenth of an inch in diameter, attached perpendicular to the sheet surface approximately 0.175 inches apart. Set B are identically spaced rods which extend parallel to the sheet and curve on a one-half inch radius at their very ends to brazed points of contact at normal incidence. Using this arrangement to induce flexural waves in a thin stainless steel strip approximately 25 mm wide by 0.3 mm thick and 30 cm long, applicant found that well defined signals were obtained with the curved lead-in rods. Excitation was performed with 5-cycle tone bursts of a 100 kHz signal, ten times per second, and well defined signals were detected with a three hundred microsecond transit time. Signal definition was better when both transmitting rods of a pair were actuated both with the straight, and with the low-profile (B) pair having curved lead-in ends.

Figure 5:
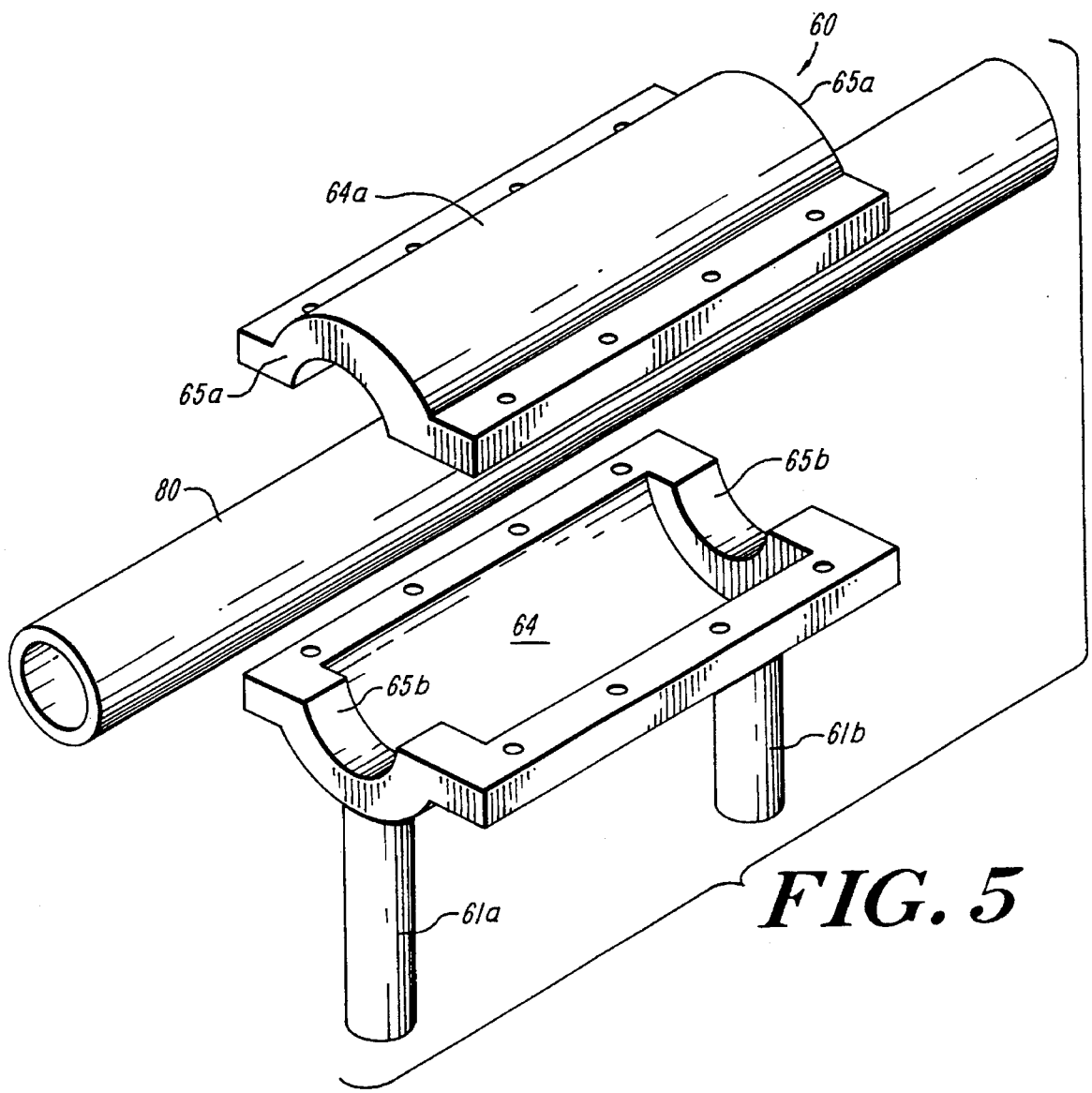
FIGS. 5, 5A and 5B illustrate another embodiment and its use for sensing in pipes or conduits.

FIG. 5 shows a related embodiment of the invention as flexural wave cell 60 adapted for sensing fluid on the inside of a cylindrical or tubular pipe or conduit 80. Embodiment 60 includes two half-housings 64a, 64b that fasten together to form a closed sleeve about the conduit. Each end of each half has a solid semi-collar or clamp ring 65a, 65b and one of the halves of the housing 64b has a transducer mount 61a, 61b in each end. As with the storage tank embodiment of FIGS. 1–3, fill and drain ports and valving may also be included in the middle, or reservoir portion of the sleeve.

Figure 5A:
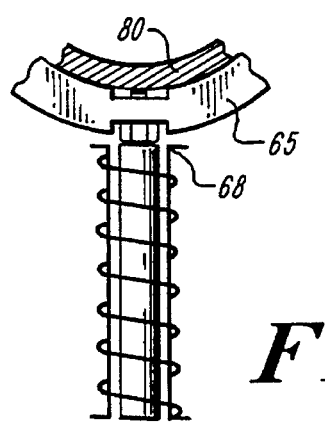
Figure 5B:
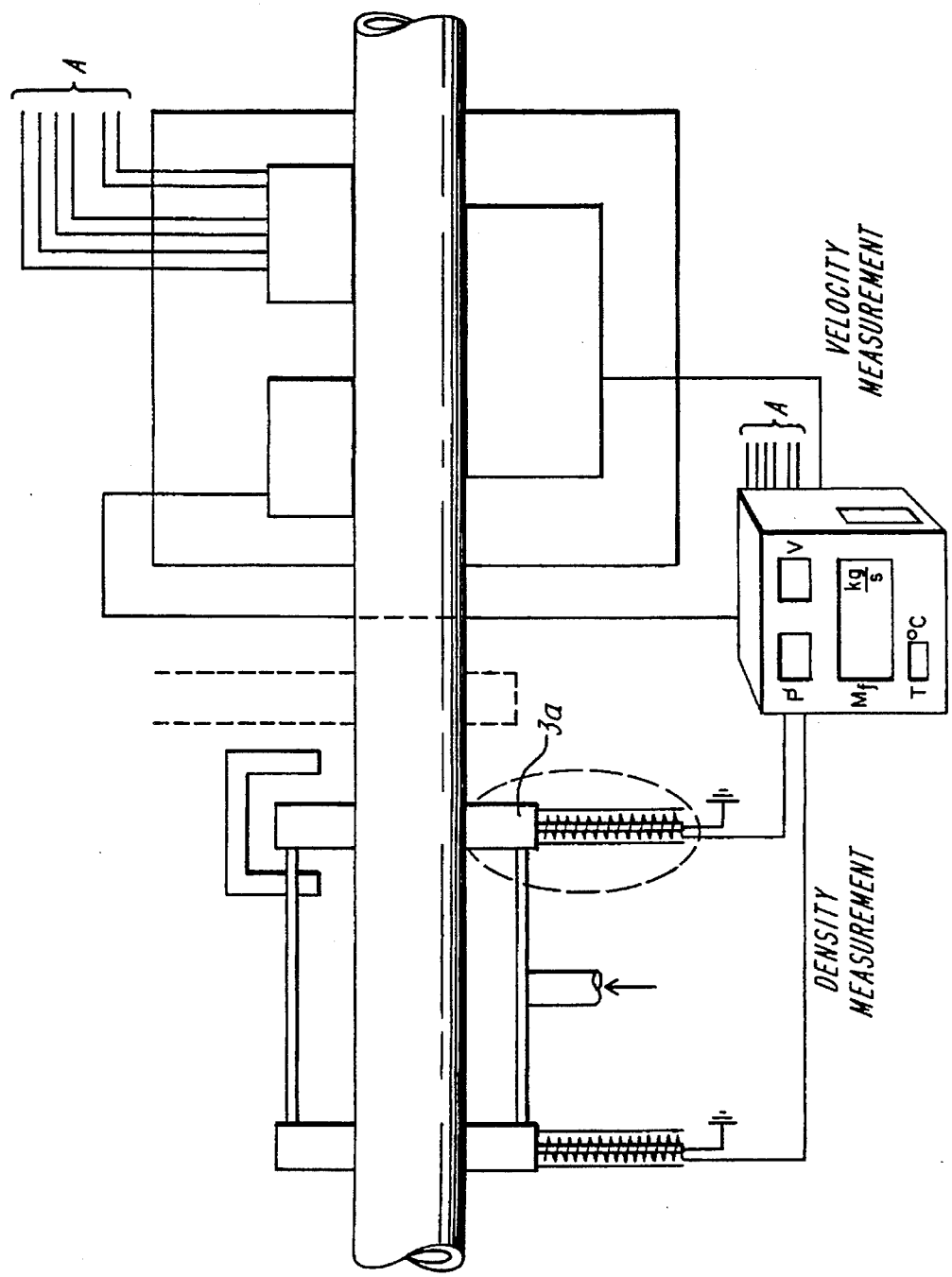

FIG. 5A illustrates a detail of one similar transducer mounting wherein the transducer rod threads into and through the collar 65 so that its tip bears against the wall of conduit 80 and is locked in place by lock nut 68. This configuration is deemed useful for larger conduits, wherein a point contact at the conduit wall may efficiently excite flexural waves. For smaller conduits (e.g. under several inches diameter), the exciting transducer does not contact the pipe, but moves the rigid collar ring 65a, 65b as a whole to induce a whip-like flexural wave in the pipe. In this case, the intermediate sleeve is formed of thin material, or may be replaced by a separate light weight envelope, leaving the end collars as physically or at least accoustically separated elements. FIG. 5B illustrates the system of FIG. 5 with associated fill and drain lines, and signal processing circuitry. This system shows a two channel intervalometer/flow meter 110 with one channel, programmed for fluid density calculations, attached to the flexural wave cell 60. The second channel of the meter is attached to a conventional clamp-on flow detection system. Used in this fashion, the system measures flow and density simultaneously, thus providing a measure of mass flow.

Such a system may be used, for example, with advantage in large refining conduits, where high flows of hot oils present difficult measurement problems. In this case the closed sleeve about the conduit serves largely to prevent the test length of pipe from corrosion, soiling or inadvertent painting which would alter its energy propagation characteristics. However it may also serve to provide reference fluid coatings to normalize the detected signal calculation for a given product.

Figure 6:
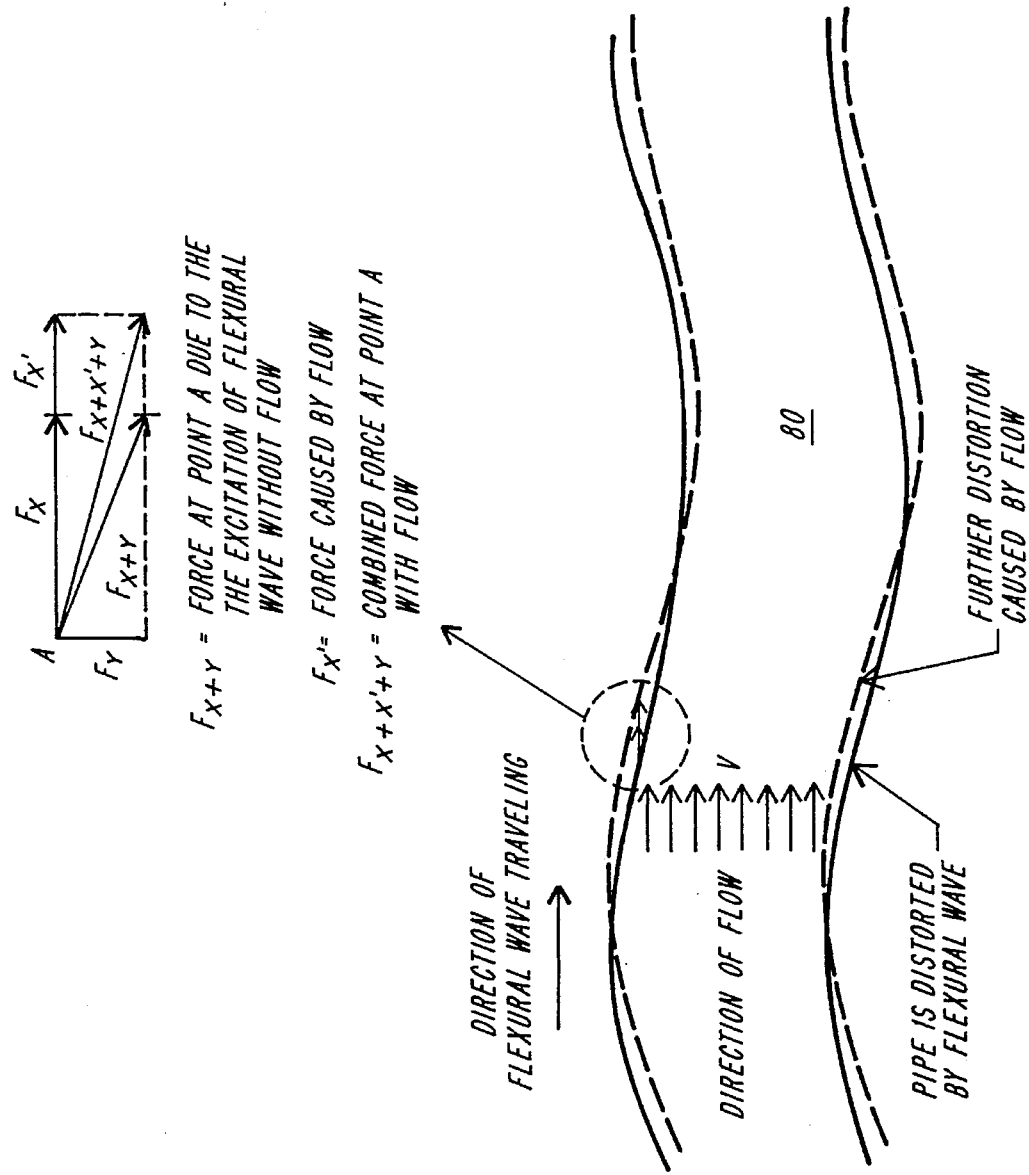
FIG. 6, 6A, 6B and 6C illustrate flow sensing with flexural waves in accordance with the present invention.
Figure 6A:
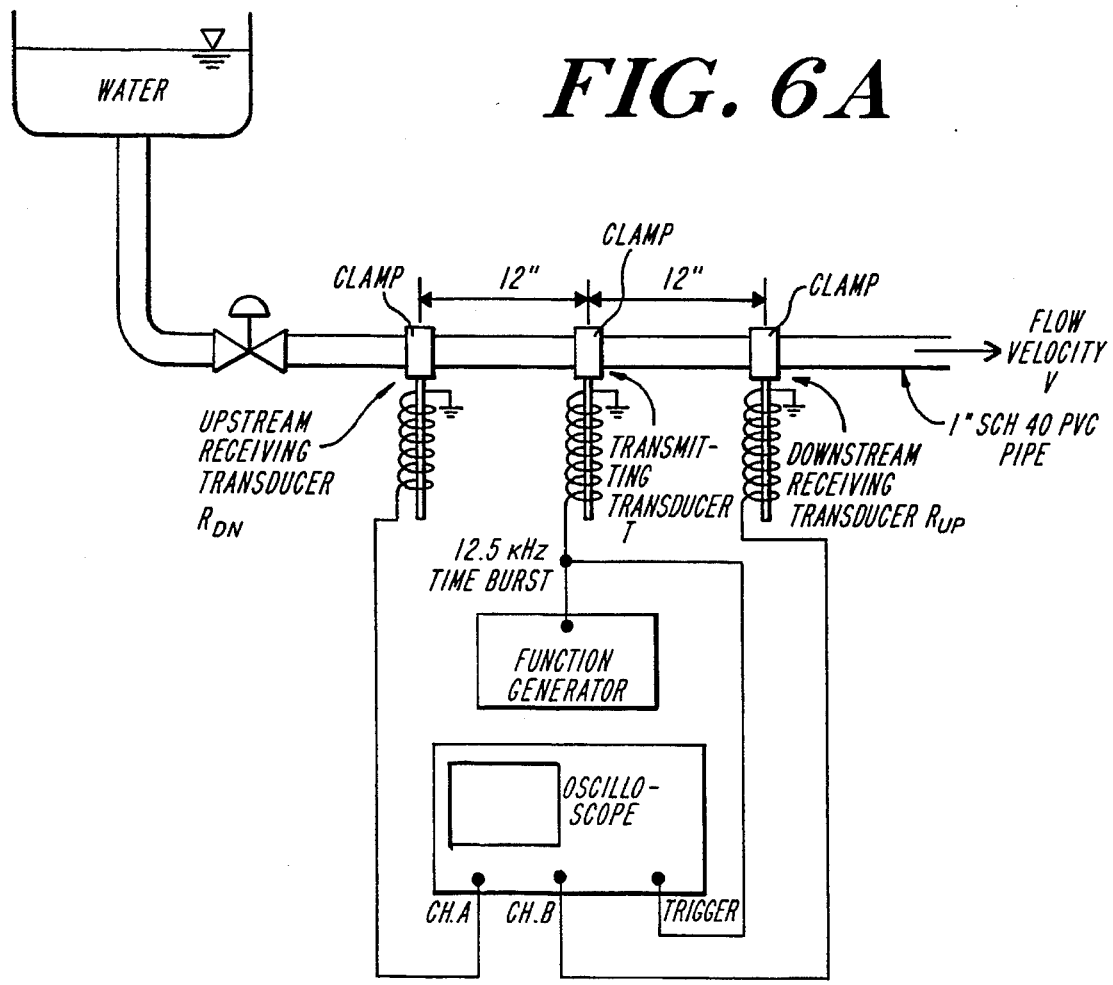
Figure 6B:
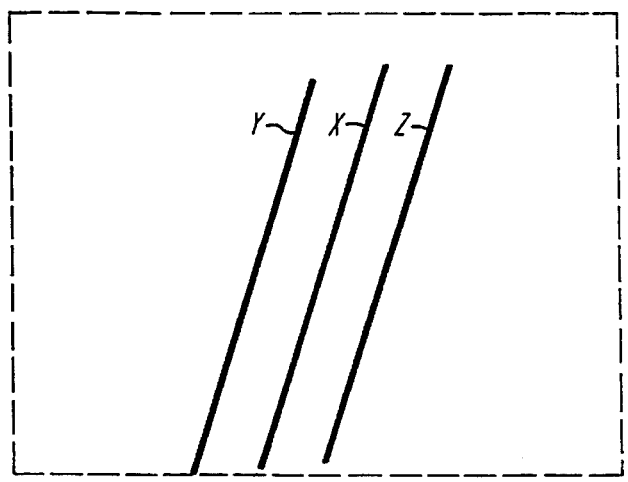

FIG. 6 models the effect of flow on flexural wave propagation in a conduit 80, which results in increasing the propagation speed when a wave is travelling in the direction of flow. The propagation speed is reduced when the flexural wave travels opposite to the direction of flow. FIG. 6A shows a flexural wave detection system of the present invention configured as a flow meter. Three clamp-on transducer collars as described above are attached to a pipe having uniform flexural characteristics, a central one being a transmitter, and the other two being an upstream receiver and a downstream receiver, these latter two being equidistant at a distance of one foot from the transmitter. Using 12.5 kHz tone bursts on one inch schedule 40 PVC pipe containing an inviscid fluid (water), the difference in upstream and downstream transit times was found to be a well-defined and easily detected essentially linear function of flow velocity. FIG. 6B shows the detected signal transit time for both receivers under no-flow conditions (trace X) and the corresponding time shift between downstream (trace Y) and upstream (trace Z) receiving transducers when flow was initiated. The system, by measuring in both directions either simultaneously or separately (sequentially), cancels out the effect of flow on $C_{flex}$. This would be more important for low density (elastomeric or plastic) tubes and less important for steel pipes.

In fact, applicant has observed that if the difference in flexural wave transit time for a conduit empty and full is more than about 10% of the nominal flexural transit time, then the contribution from fluid flow will also be significant. The PVC pipe described above had a $\Delta t_{no\ flow}$ of approximately twenty percent, and the phase velocity varied by an additional ± several percent when the liquid was flowing, the polarity being dependent on the direction of flow, at ordinary flow rates of up to three meters/second. In general, for $\Delta t_{no\ flow}$ greater than about ten percent of the flexural wave velocity, the difference between upstream and downstream transit times is expected to provide a significant time interval that is a reliable measurement of flow velocity. These conditions obtain if the density of liquid in the conduit is comparable to the of the conduit. Conversely, if the pipe density is substantially greater than the density of liquid contained therein, then $\Delta t_{flow} \ll 1\%$ and flow velocity cannot be readily determined from the flexural waves. This was found to be the case for one inch steel pipe, as well as for a number of other metal conduits of various sizes on which applicant measured the correlation of flow rate with flexural wave transit time.

Thus, according to one aspect of the present invention, a sensing system is specially adapted for sensing in low-density or light weight conduit and includes a transducer arrangement for taking bidirectional flexural wave transit time measurements, and a processor that cancels out the net flow effect to produce a $\Delta t$ indicative of the density of fluid in the conduit. It should be noted that the delay effects of flexural wave transmission may vary between conduits of similar size, and depend somewhat on the surface roughness of the conduit. For example, by intentionally roughening the surface of a conduit carrying water, a greater $\Delta t$ is observed. Thus, in a given system, sensitivity can be controlled or enhanced by polishing or roughening the conduit's inner surface. Microscopic surface texture (e.g. tire treads or "sawtooth" patterning) may also be used to increase $\Delta t$. The invention further comtemplates high sensitivity flexural wave flow cells formed of stiff low density material.

Furthermore, in any of the foregoing flexural wave sensing systems, temperature-dependent corrections may be made, and the temperature may be sensed, for example, by Rayleigh wave ultrasonic thermometry. In this case a reservoir cover used for the flexural sensing system may also protect the Rayleigh sensing path.

In the pipe-sensing situation described just above (that is, pipe density not much greater than fluid density), the transit time $\Delta t$ will be highly dependent on fluid density, so that after correction for flow velocity the $\Delta t_{fluid}$ provides a sensitive measurement of the density of the product.

Figure 6C:
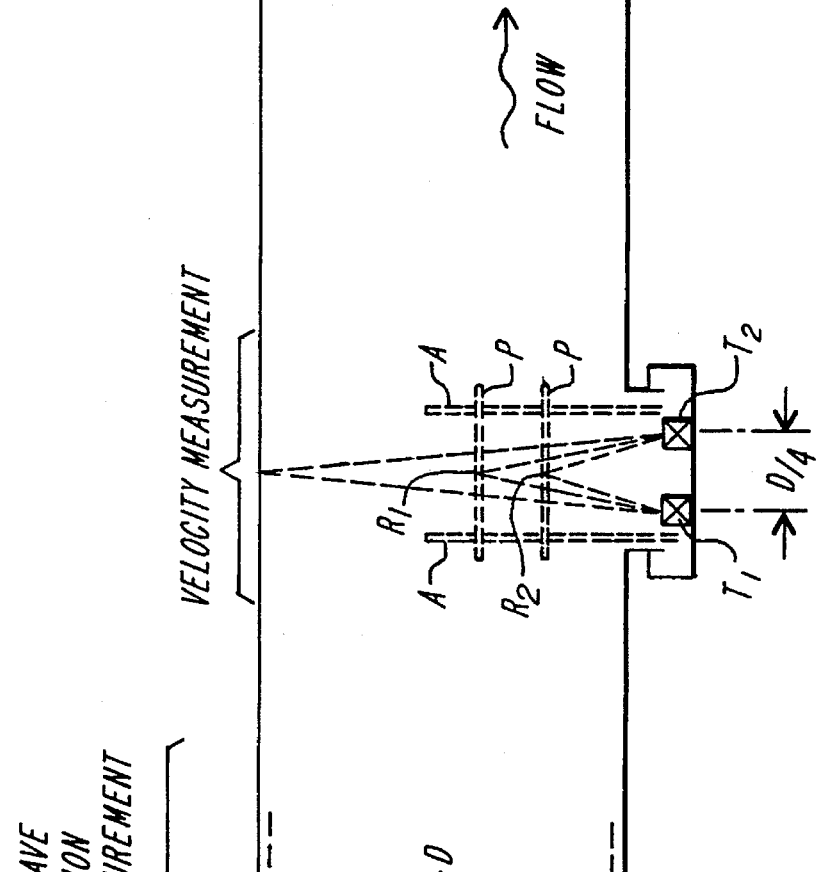

One preferred system of this sort has a flow sensor as shown in FIG. 6C. Here two sensors/transducers $T_1$, $T_2$ are mounted in a wetted mount of a precision mass flowmeter spoolpiece mounted in a pipe of diameter D, at a spacing less than approximately $D/4$ in the direction of flow, where by way of example, the diameter D may be from about four to about twelve or sixteen inches. The transducers are acoustically isolated from each other, which may be accomplished by mounting in isolation rings of a silicone rubber that is highly absorbing, at the transducer frequency, and each transducer is of a damped construction that operates well to both send and to receive signals in the fluid. Transducers $T_1$ and $T_2$ are each operated alternately to send and receive signals along upstream and downstream V-paths bounced off the opposite pipe wall. When the pipe wall has poor reflectivity, one or more reflector assemblies $R_1$, $R_2$ may be used, as indicated in phantom, to provide reflected signals representative of the average flow velocity across a portion of the flow path. Each reflector includes a stiff reflective plate P (e.g., a corrosion and build up resistent teflon-coated titanium plate) adjustably mounted on a set of support arms A.

It should be noted that in the example illustrated in FIG. 6A, the PVC pipe material was of approximately the same density as that of the measured fluid, and the low 12.5 kHz excitation frequency was effective to preserve flexural wave energy without substantial loss by a wave leakage mechanism into the fluid system. The fluid is, however, "flexed" along with the PVC pipe in sense that it is carried along as the pipe flexes. Other materials and structures will require different frequencies to maintain a guided flexural wave signal efficiency while detecting a significant flow rate to flexural propagation coupling effect.

Figure 7:
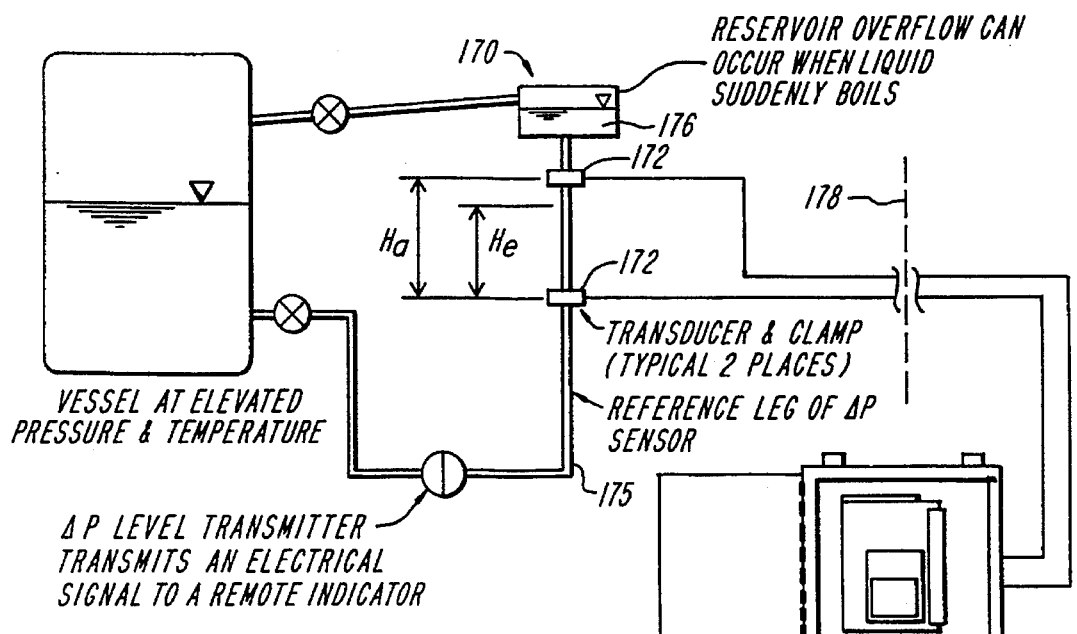
FIG. 7 illustrates an application of the embodiment of FIG. 5 to pressure sensing.

FIG. 7 illustrates another embodiment 170 of a flexural wave coupling and sensing system in accordance with the present invention. Split-collar or other flexural wave transducers 172 are shown attached to a one inch schedule 160 stainless steel pipe 175 with a wall thickness of approximately six millimeters. Pipe 175 is illustrated as the reference leg of a $\Delta P$ sensor associated with a pressure boundary 178. This particular application presents a number of challenges to a measurement system, inasmuch as the condition of interest—a sudden pressure drop that may initiate boiling and lead to overflow or vapor-induced control problems—may depend on many system states and parameters. However applicant has found the phase delay of flexural waves propagating in the conduit, when filled with an inviscid fluid, to be a substantially linear function of the density of the fluid contacting the pipe for small void fractions on the order of 1%. The measurement system of FIG. 7 utilizes this observation to detect, not $\Delta P$ per se, but the initiation of a phase transition, boiling, which is characterized by the sudden formation of microbubbles in the fluid column, resulting in a corresponding drop in fluid density.

In preliminary measurements, applicant has determined that for transducers spaced x inches apart in the water-filled 1-inch schedule 160 stainless steel pipe, a decrease in transit time of 140×nanoseconds per volume percent of gas bubbles included in the column occurs at atmospheric pressure. Thus, with a spacing of several feet between the transducers 172, changes in transit time of several microseconds occur when a pressure drop at the phase change point initiates bubble formation in amounts less than one or two percent of the fluid volume. This sensor system is expected to provide a reliable indication of the alarm condition, in which an actual state measurement replaces existing system-based or model-based condition sensing alarms. Furthermore, the electrical leadwires to an electromagnetic, piezoelectric or magnetostrictive rod transducer as described above, may be readily configured to pass through the pressure boundary 178, so that all circuits may reside outside the boundary.

As in the case of the sensor systems described above, a cover or selectively filled reservoir may be provided between the sensors to protect against scale growth or allow normalizing measurements to be made under conditions of varying fluid loading of one conduit wall.

It will be understood that all embodiments of the invention heretofore described involve sensing a property of a fluid which contacts a remote side of a wall or sheet, where "remote" is here intended to mean that the fluid and the transducers, respectively, are located on opposite sides of the sheet from each other. The measurement is, in this sense, an entirely non-invasive one. It is possible, though generally not desirable, to have the transducers located on the same side as the fluid. However, for the cover or reservoir, this element is mandatory to be placed on the sheet side opposite the fluid, to control flexural wave dependence on the non-fluid bearing surface.

In one particularly interesting application, a system in accordance with the present invention may operate to detect fogging or misting of a sheet, such as a vehicle windshield, by launching and receiving Rayleigh or surface waves into the windshield. Formation of a continuous film of water on the outside of the windshield, or fogging on the inside would introduce a distinct, although relatively small, characteristic delay in transit time, and also an attenuation of the wave. This principle can also be applied to produce a dewpoint sensor in accordance with the present invention.

While all of the above examples involve static or flowing liquids, the invention also has application to sensing a static accumulation of attached solids, particularly ice on a sheet such as a wing surface or hull. Ice, while technically having both fluid rheological properties and solid characteristics such as hardness, presents a somewhat different flexural wave response owing to its ability to present different states, as a slush or liquid that adds mass or density without stiffening the skin, or as a solid that can add stiffness that affects wave propagation in an opposite sense. On runways, aircraft are subject to deicing fluids as well as to ice.

Figure 8:
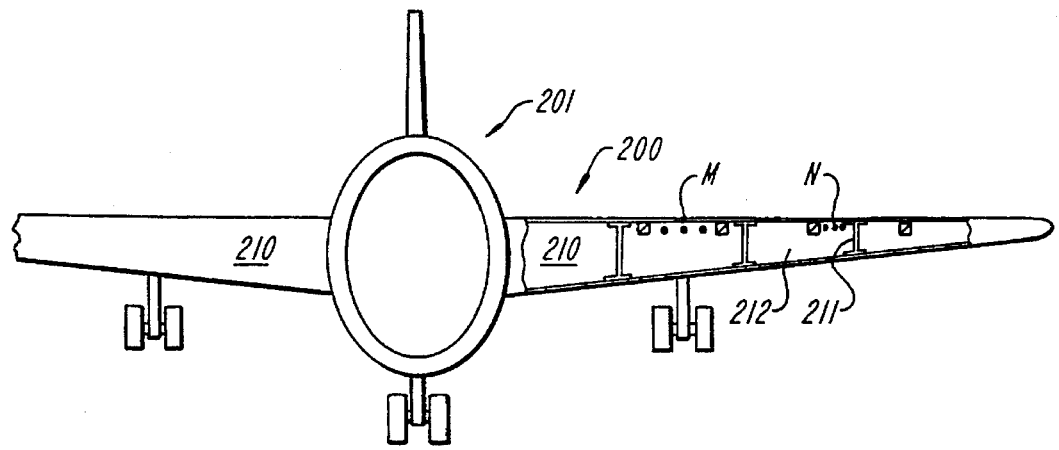
FIG. 8 and 8A illustrate another embodiment for detection of surface ice accumulations.
Figure 8A:
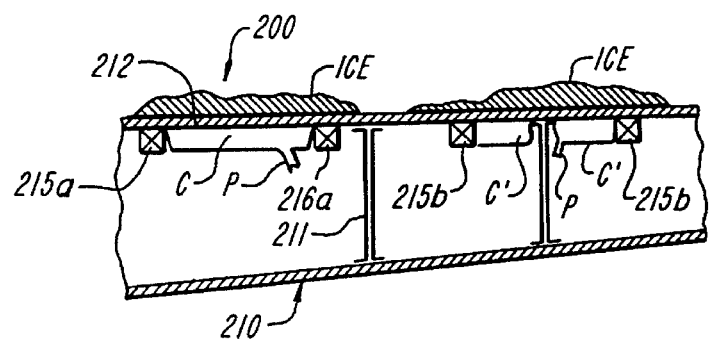

FIGS. 8, 8A illustrate an icing detector 200 in accordance with the present invention configured for use on the wing 210 of an aircraft 201. FIG. 8 shows the aircraft in schematic cross-section, with wing 210 constructed generally of external sheet portions 212 and internal structural members 211 such as struts and trusses, that collectively divide the small interior space into a number of compartments, passages and conduits that typically house the fuel tanks, control lines and mechanical, fuel, and power accessory systems. As is well known in the aircraft industry, the large surface areas of exposed metal sheet 212 may accumulate ice, particularly when the aircraft sits on a runway, and the extent of accumulation may alter the aerodynamic lift characteristics of the wing, affect control motions, and eventually add large amounts of weight to the craft. In accordance with the present invention, flexural wave cells M, N are mounted to the undersurface of the wing skin 212 to launch and detect flexural waves, which are processed as described below.

As shown in greater detail in FIG. 8A, the sensing cells M, N each contain transmitting and receiving transducers 215a, 215b and 216a 216b that define flexural wave sensing paths therebetween, with a fillable fluid cell C, C' covering the underside of the sheet between the launching and receiving transducers, and one or more valved ports P connected for filling and emptying the cells. An inlet port may connect to a high pressure fuel line, so that no additional components beyond a fuel line and control valve are required for operation of the system, while an outlet port may drain directly through an opening in the wing.

Preferably the transducers are set up to define signal paths extending over a major region of interest of the wing, with one or more cells defining flexural wave paths that are several feet or meters long. The presence of solid ice buildup introduces a variation in wave transit time that changes with ice thickness. Like the long-path measurement of fill height in a storage tank, the delay is also a function of the relative proportion of the sensing path that is covered. Thus, the flexural wave delay between spaced-apart transducers represents an integrated function of total ice accumulation over the sensing path. By using pairs of actuating rods or transducer elements contacting the skin next to each other (as shown in FIG. 4) the sensing path segments may be made highly directional, so that the extent of icing in precisely defined regions of the wing is determined.

The foregoing system will be seen to offer a distinct advantage over a prior art ice sensor that can detect ice only at the fixed point where it is mounted, or that require mounting through holes in the wing surface.

Use of the cells C, C' differs here from the situation described for storage tank measurements, in that the presence of a fill fluid F in a cell C will, in general, introduce a different phase delay than will the presence of a solid crust of ice on the remote (outer) surface of the wing. However, the amount of the delay effect (as between filled and unfilled reservoir C) may be expected to decrease as the thickness of the ice builds up on the opposite surface, so that the ratio of measured $\Delta t_{fluid}$ cell to the $\Delta t$ when no ice is present yields additional information on ice thickness. For example, as noted above, the presence of a thin hard ice layer may stiffen the wing to such an extent that transit time actually decreases. In that case, $\Delta t_{fluid}$ would introduce an opposite sign transit time change, serving to quickly identify the presence of a thin hard ice layer.

For aircraft wing application, or any embodiment of the invention that applies transducers to the underside of a horizontal sheet, the liquid reservoir may be replaced by a solid loading that is urged against the sheet surface. For example, a block of silicone rubber may be temporarily urged against the underside of the sheet to acoustically load the flexural wave interrogation path and take a normalizing reading.

As was indicated in the background description above, systems have previously been proposed in which flexural wave amplitude changes are compared to an independent compressional wave signal to determine the extent of icing. The addition of such measurements to applicant's flexural wave phase sensor, is expected to provide further information on ice accumulations, particularly for mixed or unconsolidated layers such as sleet or slush accumulations. However, even with only the normalizing loading measurements of applicant's invention providing this added information, a simple microprocessor device can make a number of comparisons of the measured and normalized conditions, and determine the presence and type of ice, as well as the approximate thickness or integrated mass over the region of the interrogation path.

In several preliminary measurements of ice buildup on thin aluminum sheeting, applicant observed a substantially linear transit time change for thickness up to several millimeters. The invention therefore yields very precise measurements of the initial rates of icing, allowing corrective action to be taken before ice loading reaches a critical level.

This completes a description of a flexural or plate wave sensing system, and representative embodiments for detecting and indicating different characteristics and practical conditions of media or materials of interest in contact with the remote side of a shell or plate forming part of a vehicle, conduit, tank or vessel. From the foregoing description it will be apparent that measurements according to these systems may be combined with other systems known in the art to extend the range of available information in diverse applications, and further variations and modifications will occur to those skilled in the art. Such variations and modifications are included within the scope of the invention, which is set forth in its various aspects and intended to be defined by the claims appended hereto.

What is claimed is:

1. An acoustic measurement system for measuring a characteristic of material contacting a sheet, the sheet having first and second sides, said system comprising means defining a sensing path extending across a region in the sheet transducer means mounted on the first side of the sheet for generating and sensing elastic wave energy signals propagated along the sensing path processing means for processing the signals to determine variations in signal propagation of said elastic wave energy signals wherein the variations depend on the characteristic of material contacting the second side of the sheet, and reference means for temporarily establishing a surface load reference condition on the first side in said region of the sheet, said processing means determining the signal propagation during said temporary surface load reference condition to identify said variations indicative of the characteristic.

2. An acoustic measurement system according to claim 1, wherein said means defining a sensing path and said reference means are included in a surface-mounted reservoir structure enclosing said region of the first side of the sheet, and including means for temporarily filling said reservoir structure to establish said surface load reference condition.

3. An acoustic measurement system according to claim 2, wherein said sheet is a containing wall, and the material is a liquid contained by said containing wall.

4. An acoustic measurement system according to claim 3, wherein the elastic wave energy signals are flexural wave energy.

5. An acoustic measurement system according to claim 4, wherein said transducer means is mounted to apply a compressional wave at normal incidence to the first side of said sheet to induce a flexural wave that travels in the sheet.

6. An acoustic measurement system according to claim 2, wherein said sheet is a metal sheet, and wherein said elastic wave energy signals are generated at a frequency selected such that phase velocity of the wave energy in the sheet is less than phase velocity of acoustic energy in the material contacting the sheet.

7. An acoustic measurement system according to claim 2, wherein the sheet is a conduit wall, and the signals are acoustic signals having a wavelength which is large compared to conduit diameter.

8. An acoustic measurement system according to claim 2, wherein the sheet is a wall of a storage tank, and the sensing path extends across a fill line of the tank.

9. An acoustic measurement system according to claim 8, wherein the sensing path extends substantially along a full fluid storage height of the tank.

10. An acoustic measurement system according to claim 2, wherein the sheet is a skin of a vessel, and said processing means determines a characteristic of ice built up on the second side of the sheet along the sensing path.

11. An acoustic measurement system according to claim 6, wherein said elastic wave energy signals are flexural wave energy at a frequency below cutoff of the higher order modes of said sheet.

12. An acoustic measurement system according to claim 1, wherein said transducer means is actuated in repetitive bursts which, in addition to launching said elastic wave energy signals along the sensing path in the sheet result in audible sounds when actuated, and is actuated with one of a plurality of burst repetition rates selected in accordance with a condition sensed by the processing means such that a repetitive pattern of said sounds audibly indicates the sensed condition.

13. An acoustic measurement system according to claim 12, wherein said sensed condition is an overfill alarm condition.

14. An acoustic measurement system according to claim 1, wherein said characteristic is density, and further comprising flow measuring means for measuring flow rate of the material contacting the sheet.

15. An acoustic sensing system for determining a characteristic of a medium contacting a solid wall said system comprising a transmitting transducer secured to one side of the wall for launching a flexural wave therein, wherein said one side is remote from a side contacting the medium a receiving transducer secured to said one side and spaced from said transmitting transducer for detecting the flexural wave traveling in said wall from the transmitting transducer and producing a signal indicative thereof an interval processor for determining a flexural wave transit time measurement, wherein the transmitting transducer launches a lowest order asymmetric flexural wave such that the signal produced by the receiving transducer is well-defined along a saled signal path, and means responsive to said transit time measurement for determining the characteristic of the medium.

16. An acoustic sensing system according to claim 15, wherein the characteristic is fill height.

17. An acoustic sensing system according to claim 15, wherein the characteristic is phase transition.

18. An acoustic sensing system according to claim 15, wherein the characteristic is density.

19. An acoustic sensing system according to claim 15, wherein the characteristic is thickness.

20. An acoustic sensing system according to claim 15, wherein the characteristic is integrated mass.

21. An acoustic measurement system for measuring a characteristic of material contacting a sheet, the sheet having opposed first and second sides, said system comprising means defining a sensing path extending across a region in the sheet a pair of transducers mounted on the first side of the sheet for generating and sensing elastic wave energy signals propagated along the sensing path processing means for processing the signals to determine the characteristic of material contacting the second side of the sheet, and cover means placed over the first side of the sheet over the region of the sensing path for providing a reference surface loading condition of said first side wherein the signals propagated along said path are processed to develop a reference timing interval, and said processing means processes a received signal in relation to said reference timing interval, that varies with contact of material on the second side.

* * * * *

UNITED STATES PATENT AND TRADEMARK OFFICE
CERTIFICATE OF CORRECTION

PATENT NO. : 5,456,114
DATED : October 10, 1995
INVENTOR(S) : Yi Liu and Lawrence C. Lynnworth It is certified that error appears in the above-identified patent and that said Letters Patent is hereby corrected as shown below:

At column 4, line 23, please replace "$\lambda 4$" by --a $\lambda/4$--;

At column 4, line 31, please replace "thicknes" with --thickness--;

At column 6, line 27, after "lines" please replace "8*a*, 8*b*" with --18*a*, 18*b*--;

At column 8, line 53, after "distance" please insert --,--;

At column 10, line 65, after "comparable to the" please insert --density--; and

At column 13, line 8, please replace "0n runways" with --On runways--.

Signed and Sealed this

Seventh Day of July, 1998

Attest:

BRUCE LEHMAN

*Attesting Officer*     *Commissioner of Patents and Trademarks*